(12) United States Patent
Koike et al.

(10) Patent No.: US 7,410,663 B2
(45) Date of Patent: Aug. 12, 2008

(54) OIL OR FAT COMPOSITION

(75) Inventors: Shin Koike, Tokyo (JP); Takatoshi Murase, Haga-gun (JP); Takanori Nii, Kashima-gun (JP); Toshihiro Tanaka, Wakayama (JP)

(73) Assignee: Kao Corporation, Tokyo (JP)

( * ) Notice: Subject to any disclaimer, the term of this patent is extended or adjusted under 35 U.S.C. 154(b) by 694 days.

(21) Appl. No.: 11/049,975

(22) Filed: Feb. 4, 2005

(65) Prior Publication Data

US 2005/0129830 A1 Jun. 16, 2005

Related U.S. Application Data

(63) Continuation of application No. PCT/JP03/09806, filed on Aug. 1, 2003.

(30) Foreign Application Priority Data

Aug. 7, 2002 (JP) ............................. 2002-229901

(51) Int. Cl.
A23D 9/007 (2006.01)
(52) U.S. Cl. ..................... 426/601; 424/439; 426/611
(58) Field of Classification Search ................ 426/601, 426/611; 424/439
See application file for complete search history.

(56) References Cited

U.S. PATENT DOCUMENTS

| 6,448,292 | B2 * | 9/2002 | Koike et al. ................ 514/558 |
| 6,689,812 | B2 * | 2/2004 | Peet et al. ................... 514/560 |
| 6,762,203 | B2 * | 7/2004 | Koike et al. ................. 514/546 |
| 6,844,021 | B2 * | 1/2005 | Koike et al. ................. 426/611 |
| 6,852,758 | B2 * | 2/2005 | Koike et al. ................. 514/560 |
| 7,009,661 | B2 * | 3/2006 | Sato ........................... 348/558 |
| 7,090,886 | B2 * | 8/2006 | Koike et al. ................. 426/601 |
| 7,232,586 | B2 * | 6/2007 | Nishide et al. .............. 426/601 |
| 2004/0062847 | A1 * | 4/2004 | Koike et al. ................. 426/601 |

FOREIGN PATENT DOCUMENTS

| EP | 990391 | 5/2000 |
| JP | 3-103499 | 4/1991 |
| JP | 10-57086 | 3/1998 |
| WO | WO 02/11551 A1 | 2/2002 |

OTHER PUBLICATIONS

Nakazato et al, Journal of the Japan Oil Chemists' Society, 1997, vol. 46, No. 7, pp. 51-55 (w/English abstract).

* cited by examiner

*Primary Examiner*—Carolyn Paden
(74) *Attorney, Agent, or Firm*—Oblon, Spivak, McClelland, Maier & Neustadt, P.C.

(57) ABSTRACT

The present invention relates to an oil or fat composition containing the following components (A) and (B):
(A) from 80 to 99.9 wt. % of a monoglyceride containing 20 to 75 wt. % of docosahexaenoic acid (DHA) and 0.1 to 25 wt. % of icosapentaenoic acid (IPA), as the constituent fatty acids thereof, wherein the weight ratio of DHA/IPA being 2 or more; and
(B) from 0.1 to 20 wt. % of a diglyceride.

19 Claims, No Drawings

OIL OR FAT COMPOSITION

CROSS-REFERENCE TO A RELATED APPLICATION

The present application is a continuation of International Application PCT/JP03/09806 filed on Aug. 1, 2003, which claims priority to Japanese Patent Application No. 2002-229901, filed Aug. 7, 2002.

FIELD OF THE INVENTION

The present invention relates to oil or fat compositions which have a specific glyceride composition and a specific fatty acid composition containing docosahexaenoic acid and icosapentaenoic acid as the constituent fatty acids.

BACKGROUND OF THE INVENTION

With the recent trend toward a healthy life style and a growing demand for a preventive remedy of diseases, a number of research have been made on the health-improving functions of fish oils or components thereof such as icosapentaenoic acid (C20:5, which will hereinafter be abbreviated as "IPA") and docosahexaenoic acid (C22:6, which will hereinafter be abbreviated as "DHA"). Specifically, anti-arteriosclerotic effects, cerebral function improving effects, visual function improving effects, antitumor effects and anti-inflammatory effects are known (Journal of Oleo Science, 48, 1017(1999) and the like).

These components have a strong rancid odor upon storage, so the practical application of an oil or fat composition containing such a component is therefore extremely limited for its flavor. In addition, it has been pointed out that IPA has inhibitory effects on platelet aggregation or abilities to prolong the bleeding time. (Atherosclerosis, 50, 3-10(1984), Lipids, 32, 1129-1136(1997)).

On the other hand, the present inventors have found that ω3 unsaturated monoglycerides-diglycerides including IPA and DHA have a body fat burning activity (JP2001-64672 A). They have also found that monoglycerides, especially IPA monoglycerides have high PPAR activating effects (JP2001-354558 A). But the PPAR activating effects of DHA monoglyceride remain to be elucidated.

The term "PPAR" as used herein means one of the nuclear receptors which is activated by a peroxisome proliferator (PPAR: Peroxisome Proliferator Activated Receptor). Recent studies have revealed that PPAR takes part in a number of physiological or pathological phenomena. Since fibrate compounds which are curative pharmaceuticals for hyperlipidemia and thiazolidine derivatives known for the treatment of diabetes were found to be PPAR agonists, attempts have been made to develop other new drugs for alleviating hyperlipidemia or insulin-resistant diabetes (The Cell, 31(6), 218-234 (1999), J. Lipid Res. 37, 907-925(1996), Curr. Opin. Lipidol. 10, 151-159(1999)).

In addition, various technologies relating to monoglycerides have been disclosed. Preparation processes of monoglycerides are disclosed, for example, in JP-A-Hei 3-103499, JP-A-Hei 8-214892, JP-A-Hei 10-57086, JP2000-212588 A and JP2001-329291 A. In JP-A-Hei 7-39302, monoglycerides containing a highly unsaturated fatty acid are disclosed. These monoglycerides are nevertheless not satisfactory in their flavor.

In JP-A-Hei 8-60181 and JP-A-Hei 10-265795, oil or fat compositions containing partial glycerides including monoglycerides are disclosed. These compositions are composed mainly of diglycerides so that dispersibility in water is superior to those composed mainly of triglycerides. Owing to a low monoglycerides content, however, these compositions involve problems of processability, such as impossibility of incorporating water therein.

As described above, it has been elucidated that oil or fat compositions containing IPA or DHA have a variety of health functions. Yet they have problems of processability, flavor, and the like and technologies capable of overcoming these problems remain to be established.

From such viewpoints, there is a growing demand for the development of an oil or fat composition having good processability and flavor as a food, and having excellent physiological effects.

SUMMARY OF THE INVENTION

In one aspect of the present invention, there is thus provided an oil or fat composition containing the following components (A) and (B):

(A) from 80 to 99.9 wt. % of a monoglyceride containing 20 to 75 wt. % of docosahexaenoic acid (DHA) and 0.1 to 25 wt. % of icosapentaenoic acid (IPA), as the constituent fatty acids thereof, wherein the weight ratio of DHA/IPA being 2 or more, and (B) from 0.1 to 20 wt. % of a diglyceride.

In another aspect of the present invention, there is also provided a food, animal feed or pharmaceutical product containing the above-described oil or fat composition.

DETAILED DESCRIPTION OF THE INVENTION

The present inventors have carried out a variety of investigations on the fatty acid composition of a monoglyceride. As a result, it has been found that a monoglyceride mixture containing specific amounts of IPA and DHA as constituent fatty acids has a good flavor, excellent processability owing to remarkable gelling properties, water-absorbing capabilities, potent PPAR activating effects and β oxidation activating effects and is therefore useful as a food, animal feed or pharmaceutical product beneficial for health.

The content of docosahexanoeic acid (DHA) in the fatty acids constituting the monoglyceride (Component (A)) of the oil or fat composition of the invention is preferably from 20 to 75 wt. %, more preferably from 30 to 65 wt. %, even more preferably from 35 to 55 wt. % from the viewpoints of physiological effects, processability and flavor.

The content of icosapentaenoic acid (IPA) in the fatty acids constituting the monoglyceride (Component (A)) is preferably from 0.1 to 25 wt. %, more preferably from 0.1 to 20 wt. %, even more preferably from 0.1 to 15 wt. % from the viewpoints of physiological effects, processability and flavor.

The weight ratio of DHA to IPA (DHA/IPA) in the monoglyceride is required to be 2 or greater, preferably from 2 to 20, more preferably from 3 to 13, still more preferably from 4 to 11, yet still more preferably from 5 to 8 from the viewpoints of flavor, processability and physiological effects.

The monoglyceride (Component (A)) may further contain, as the other constituent fatty acids thereof, ω9 unsaturated fatty acids, ω6 unsaturated fatty acids, saturated fatty acids and the like. For example, the ω9 unsaturated fatty acid having from 8 to 22 carbon atoms such as oleic acid is contained preferably in an amount of from 0 to 50 wt. %, more preferably from 0.1 to 25 wt. %, even more preferably from 0.1 to 15 wt. % from the viewpoints of intake balance of fatty acids and industrial productivity of the oil or fat.

The ω6 unsaturated fatty acid having from 8 to 22 carbon atoms such as linoleic acid or γ-linolenic acid is contained preferably in an amount of from 0.1 to 25 wt. %, more preferably from 0.1 to 10 wt. %, even more preferably from 0.2 to 5 wt. % from the viewpoints of intake balance of fatty acids and industrial productivity of the oil or fat.

The saturated fatty acid is contained preferably in an amount of from 0 to 30 wt. %, more preferably from 0.1 to 20 wt. %, even more preferably from 0.5 to 15 wt. % from the viewpoints of physiological effects and industrial productivity of the oil or fat.

Such a monoglyceride (Component (A)) is contained in the oil or fat composition of the present invention in an amount of from 80 to 99.9 wt. %, preferably from 90 to 99 wt. %, more preferably from 92.9 to 97 wt. %, even more preferably from 93 to 97 wt. % from the viewpoints of physiological effects and processability.

The diglyceride (Component (B)) is contained in the oil or fat composition of the present invention in an amount of from 0.1 to 20 wt. %, preferably from 1 to 10 wt. %, more preferably from 2.9 to 7 wt. %, even more preferably from 3 to 7 wt. % from the viewpoints of processability, flavor and industrial productivity of the oil or fat.

The constituent fatty acids of the diglyceride (Component (B)) are preferably similar to those of the monoglyceride from the viewpoint of industrial productivity of the oil or fat.

In the oil or fat composition of the present invention, the content of a triglyceride is preferably 19.9 wt. % or less, more preferably from 0 to 9 wt. %, even more preferably from 0.01 to 4 wt. %, still more preferably from 0.1 to 4 wt. % from the viewpoints of physiological effects, processability and industrial productivity of the oil or fat.

The constituent fatty acids of the triglyceride are preferably similar to those of the monoglyceride from the viewpoint of industrial productivity of the oil or fat.

In the oil or fat composition of the present invention, the content of a free fatty acid or salt thereof is preferably 5 wt. % or less, more preferably from 0 to 2.5 wt. %, even more preferably from 0.01 to 1 wt. %, still more preferably from 0.1 to 0.5 wt. % from the viewpoints of flavor, stability and industrial productivity of the oil or fat.

The free fatty acid or salt thereof contained in the oil or fat composition of the present invention are preferably similar to the constituent fatty acids of the monoglyceride from the viewpoint of industrial productivity of the oil or fat.

The oil or fat composition of the present invention having such a specific glyceride composition and a specific fatty acid composition as the constituent fatty acids may be prepared, for example, by esterification between glycerin and a fatty acid in the presence of an enzyme such as lipase or transesterification between glycerin and an oil or fat in the presence of an alkali catalyst. As described later in the preparation example, the target oil or fat composition may also be prepared by binding a protecting group such as dioxolane to glycerin, performing transesterification with an oil or fat, and then removing the protecting group from the reaction product.

The oil or fat composition of the present invention is preferably used after refining such as degumming, deacidification, washing with water, decoloration, deodorization and the like from the standpoints of flavor and stability. In particular, its peroxide value (POV) of the oil or fat is adjusted to 20 or less, preferably 10 or less, more preferably 7 or less, even more preferably 5 or less, still more preferably 3 or less, yet still more preferably from 0.1 to 1. The color (10R+Y) of the oil or fat as measured by the Lovibond method (using a 5.25-inch glass cell) is preferably adjusted to 50 or less, more preferably 40 or less, still more preferably 30 or less, yet still more preferably from 5 to 25.

Addition of an antioxidant (Component (C)) to the oil or fat composition of the present invention is preferable in view of flavor and stability. Any antioxidant is usable insofar as it is commonly added to foods and pharmaceuticals. As the antioxidant, catechin, tocopherol, vitamin C fatty acid esters, butylated hydroxytoluene (BHT), butylated hydroxyanisole (BHA), tertiary butylated hydroquinone (TBHQ), phospholipids and natural antioxidant components may be used either singly or in combination. Of them, tocopherol and catechin are preferred. Examples of the vitamin C fatty acid esters include palmitate esters and stearate esters, while those of the natural antioxidant components include herbs such as rosemary and extracts from the leaves or roots of a peach. The antioxidant is added to the oil or fat composition of the present invention preferably in an amount of from 0.01 to 5 wt. %, more preferably from 0.05 to 1 wt. %.

In order to lower the cholesterol level, a phytosterol (Component (D)) is preferably added to the oil or fat composition of the present invention. The phytosterol content in the oil or fat composition of the present invention is preferably from 0.05 to 19.9 wt. %, more preferably from 0.3 to 4.7 wt. %, even more preferably from 1.2 to 4.7 wt. %. Examples of the phytosterol include that in free form such as α-sitosterol, β-sitosterol, stigmasterol, campesterol, α-sitostanol, β-sitostanol, stigmastanol, campestanol and cycloartenol; and that in ester form such as their fatty acid esters, ferulate esters and cinnamate esters.

It is more preferred to add a crystallization inhibitor to the oil or fat composition of the present invention in order to improve the appearance and working efficiency. Examples of the crystallization inhibitor used in the present invention include polyol fatty acid esters such as polyglycerin-condensed ricinoleic acid esters, polyglycerin fatty acid esters, sucrose fatty acid esters, sorbitan fatty acid esters, polyoxyethylene sorbitan fatty acid esters, and propylene glycol fatty acid esters. As the polyol fatty acid esters, polyglycerin fatty acid esters, sucrose fatty acid esters and sorbitan fatty acid esters each having an HLB (calculation formula of Griffin) of 4 or less, preferably 3 or less, may be used. The crystallization inhibitor is added to the oil/fat composition of the present invention preferably in an amount of from 0.02 to 5 wt. %, more preferably from 0.05 to 2 wt. %.

The oil/fat composition thus obtained exhibits remarkably excellent PPAR activating effects and β oxidation activating effects, and in addition, owing to its good gelling properties and water-absorbing capabilities, has excellent processability and flavor. Owing to such excellent properties, the oil or fat composition of the present invention is suited for use in foods, animal feed and pharmaceuticals.

The oil or fat composition of the present invention may be used for oil/fat-containing foods or food additives containing the composition as a part of the food. Healthy foods which perform a special function to promote health can be given as an example of such oil/fat-containing foods. As food additives, the composition may be used as an emulsifier, quality improver or the like for the purpose of emulsification, demulsification, solubilization, dispersing, wetting, coating, foaming, antifoaming, penetration, mold release, washing, inhibition of bacterial growth or quality improvement.

Specific examples of food include capsules, tablets, granules, powder, bakery foods such as bread, cake, cookies, pie, pizza crust and bakery mix, oil-in-water type emulsified foods such as soup, sauce, ice cream, coffee cream, dressing, mayonnaise and whip cream, water-in-oil type emulsified foods such as margarine, spread and butter cream, confections such as chocolate, candy, caramel and candy tablet, processed meat products such as sausage, ham and hamburger steak, beverages, noodles, prepared foods, frozen foods, and retort foods. The above-exemplified oil/fat-containing food may be prepared by adding, in addition to the above-described oil or fat composition, raw materials ordinarily employed for the oil/fat-containing food or food additive depending on the kind thereof.

The amount of the oil or fat composition of the present invention to be added to the oil/fat-containing food varies depending on the kind of food, but is preferably from 0.1 to 100 wt. %, more preferably from 1 to 80 wt. %. The amount of the oil or fat composition of the present invention to be added to the food additive varies depending on the purpose of use of the food additive, but is preferably from 1 to 100 wt. %, more preferably from 80 to 100 wt. %. The amount of the food additive of the present invention to be added to food varies depending on the purpose of use of the food additive, but is preferably from 0.01 to 10 wt. %, more preferably from 0.1 to 5 wt. %.

The pharmaceuticals containing the oil/fat composition of the present invention include those for oral administration. Specific examples include solid preparations such as powder, granules, capsules, pills, and tablets and liquid preparations such as solutions, suspensions, and emulsions. These orally administrable pharmaceuticals may be prepared by adding, in addition to the oil or fat composition of the present invention, any of the additives such as vehicles, disintegrants, binders, lubricants, surfactants, alcohols, water, water-soluble polymers, sweetening agents, taste corrigents, and sour agents, which are generally used in accordance with the form of the pharmaceutical. Examples of the orally administrable pharmaceuticals include diabetes preventive remedies, obesity preventive remedies and hyperlipidemia preventive remedies, each of which utilizes the PPAR activating effects and β oxidation activating effects of the composition. Although the content of the oil or fat composition of the present invention in the orally administrable pharmaceutical varies depending on the purpose of use and form of the pharmaceutical, it is preferably from 0.1 to 100 wt. %, more preferably from 1 to 80 wt. %. The oil or fat composition is administered preferably at a daily dose of from 0.1 to 50 g in one to several portions.

Examples of animal feed include not only feed for animals such as pig, chicken and fish, but also pet food for dogs, cats and the like. The amount of the oil or fat composition of the present invention to be added to the feed is preferably from 1 to 40 wt. %, more preferably from 1 to 30 wt. %, even more preferably from 2 to 20 wt. %. A portion or all of the oil or fat in the feed may be replaced by the oil or fat composition of the present invention.

Such animal feed may be prepared by mixing the above-described oil or fat composition with raw materials ordinarily used for animal feed such as meats, proteins, grains, brans, lees, saccharides, vegetables, vitamins and minerals. Examples of meat include livestock or animal meat such as beef, pork, mutton, lamb, rabbit meat, and kangaroo meat and byproducts or processed products thereof; products obtained by rendering the above-exemplified raw meat such as meat balls, meat bone meals and chicken meal; and fish meat such as bluefin tuna, bonito, horse mackerel, sardine, scallop, turban shell and fish meal. Examples of the proteins include milk proteins such as casein and whey, and vegetable proteins such as soybean protein; those of the grains include wheat, barley, rye, milo, and corn; those of the brans include rice bran and wheat bran, and those of the lees include soybean lees. The total content of the meat, proteins, grains, brans, and lees is preferably from 5 to 95% of the animal feed. Examples of the saccharides include glucose, oligosaccharide, sugar, molasses, starch and liquid sugar and their content is preferably from 5 to 80 wt. %. As the vegetables, vegetable extracts are usable and its content in the animal feed is preferably from 1 to 30 wt. %. Examples of the vitamins include A, $B_1$, $B_2$, D, E, niacin, pantothenic acid and carotene and their content in the animal feed is preferably from 0.05 to 10 wt. %. Examples of the minerals include calcium, phosphorus, sodium, potassium, iron, magnesium and zinc and their content in the animal feed is preferably from 0.05 to 10 wt. %. In addition, the animal feed of the present invention may contain ordinarily employed additives therefor such as a gelling agent, shape retainer, pH regulator, seasoning, antiseptic and nutrition supplement.

EXAMPLES

The following examples further describe and demonstrate embodiments of the present invention. The examples are given solely for the purpose of illustration and are not to be construed as limitations of the present invention.

Example 1

Preparation of Oil or Fat Compositions

Oil or fat compositions as described below were prepared. The composition of each of the resulting oil or fat compositions is shown in Table 1. The glyceride composition was measured by the HPLC method (column: "TSKgelG2500H", product of TOSOH, eluting solvent: THF, solvent flow rate: 0.4 mL/min, detector: RI), while the fatty acid composition was measured by the GLC method after methyl esterification (Japan Oil Chemists' Society "Standard Methods for the Analysis of Fats, Oils and Related Materials" 2.4.1.2-1996, 2.4.2.2-1996).

Oil or Fat Composition 1 (Example Invention Product 1)

In a four-necked flask were charged 422.9 g of 2,2-dimethyl-1,3-dioxolan-4-methanol and 0.64 g of sodium hydroxide. After dehydration at 80° C. under reduced pressure and conversion into the corresponding alcoholate, the resulting alcoholate was cooled to 50° C. To this, 355.3 g of a DHA-rich oil "DHA-22" (product of Maruha Corporation) was added and a reaction was carried out for 1.5 hours. The reaction mixture was then neutralized with 50% sulfuric acid. From the reaction mixture, water and 2,2-dimethyl-1,3-dioxolan-4-methanol were removed by distillation under reduced pressure at 1.33 kPa at from 80 to 100° C. The residue was washed with water, whereby 451.4 g of monoglyceride acetal was obtained.

To 220 g of the monoglyceride acetal thus obtained was added 13.2 g of acid clay ("GALLEON EARTH"; product of Mizusawa Industrial Chemicals). Deacetalization was effected for 6 hours (at 70° C. and 13.3 kPa) while introducing water vapor in an amount of 10% per hour relative to the monoglyceride acetal into the reaction system to remove acetone generated upon reaction and excessive water vapor out of the system. After the addition of 6.6 g of an acid adsorbent ("KW600S", product of Kyowa Chemical Industry), dehydration was conducted for 0.5 hour (at 6.65 kPa and 70° C.), followed by filtration, whereby 170.7 g of a monoglyceride was obtained. To the resulting monoglyceride was added 200 ppm of "E-mix D" (tocopherol, product of Eisai) to prepare an Oil or Fat Composition 1.

Oil or Fat Composition 2 (Example Invention Product)

In a similar manner to that employed for the preparation of the Oil or Fat Composition 1 except for the use of "DHA-45" (product of Maruha Corporation) as the DHA-rich oil, an Oil or Fat Composition 2 was prepared.

Oil or Fat Composition 3 (Example Invention Product)

In a four-necked flask were charged 1000 g of DHA-rich oil "DHA-70G" (product of Nippon Kagaku Shiryo), 280 g of glycerin and 1 g of sodium hydroxide. Under a nitrogen gas stream, the mixture was reacted at 170° C. for 2 hours. After the completion of the reaction, 0.88 g of phosphoric acid was added to neutralize the reaction mixture. After deglycerolization for 10 minutes (at 180° C. and 0.667 kPa), thin film evaporation was conducted (at 185° C. and 0.004 kPa). The resulting distillate was collected, to which 200 ppm of tocopherol "E-mix D" (product of Eisai) was added, whereby an Oil or Fat Composition 3 was obtained.

Oil or Fat Composition 4 (Comparative Product)

A DHA-rich oil "DHA-22" (product of Maruha Corporation) was used as an Oil or Fat Composition 4.

Oil or Fat Composition 5 (Comparative Product)

The residue after thin film evaporation, which had been generated upon preparation of the Oil or Fat Composition 3, was collected and fractionated by silica gel chromatography ("Wakogel C-200" (product of Wako Pure Chemicals) using, as a solvent, hexane and ethyl acetate (their ratio was varied in the following order: 100:0, 95:5, 90:10, 80:20 and 70:30, each v/v). The solvent was then removed by an evaporator. The fractions thus obtained were mixed, followed by the addition of 200 ppm of "E-mix D" (tocopherol; product of Eisai) to afford an Oil or Fat Composition 5.

Oil or Fat Composition 6 (Comparative Product)

High-purity monoglyceride "EXCEL O-95R" (product of Kao) was used as an Oil or Fat Composition 6.

Oil or Fat Composition 7 (Comparative Product)

Eicosapentaenoic acid (product of Sigma) was employed.

Oil or Fat Composition 8 (Comparative Product)

Docosahexaenoic acid (product of Sigma) was employed.

Example 2

Test on PPARγ Activation

The small intestine epithelial cell line IEC-6 was inoculated on a 12 well plate and cultured in DMEM (5% FCS) for 24 hours. A plasmid (pGAL4-PPARγ-LBD) expressing the chimeric molecules of a GAL4-DNA binding domain (DBD) and a PPARγ ligand binding domain (LBD) and a reporter plasmid (pREP) containing a GAL4 binding sequence upstream of a firefly luciferase gene were introduced simultaneously by using a transfection reagent ("QIAGEN"; Superfect transfection reagent), each in an amount of 0.5 μg/well. In order to monitor the transfection efficiency, a renilla luciferase gene was incorporated in the pGAL4-PPARγ-LBD at the same time. The culture broth was then replaced with a DMEM (+250 μM BSA) medium containing a test substance (500 μM), followed by incubation for further 24 hours. After washing with PBS, the cells were lysed using dual luciferase assay system (product of Promega Corporation). To the resulting lysate was added a substrate solution containing luciferin, and firefly and renilla luciferase activities were measured by a luminometer. In the above-described manner, the PPARγ activating capacity was evaluated by measuring the transcriptional activity (luciferase activity) of the PPARγ-dependent gene. It is to be noted that the PPARγ-dependent gene transcriptional activity (luciferase activity) was defined as described below.

PPARγ-dependent gene transcriptional activity (luciferase activity)=(firefly luciferase activity by p REP)/(renilla luciferase activity by pGAL4-PPARγ-LBD).

In Table 1, PPARγ-dependent transcriptional activity by the control is set at 100 and activity relative to it is indicated.

Example 3

Evaluation of Gelling Properties

Gelling properties of a 70:30 (weight/weight) mixture of each oil or fat composition and water were visually observed and evaluated based on the below-described criteria. The results are shown in Table 1.
A: The mixture lacks fluidity and is gelled.
B: The mixture has low fluidity and is gelled slightly.
C: The mixture has fluidity and is partially gelled.
D: The mixture has fluidity and is not gelled at all.

Example 4

Evaluation of Rancid Odor

Each sample (each oil or fat composition:water=70:30) prepared in Example 3 was allowed to stand at room temperature for 1 week. The sample was smelled and organoleptic evaluation of rancid odor was performed based on the below-described criteria. The results are shown in Table 1.
A: The sample is almost free from a rancid odor and the odor does not cause discomfort.
B: The sample emits a little rancid odor, but the odor causes little discomfort.
C: The sample emits a rancid odor and the odor causes discomfort.
D: The sample emits a severe rancid odor and the odor causes extreme discomfort.

Example 5

Evaluation of Water-Absorbing Capabilities

The upper limit of the amount of water (wt. % relative to the whole system) incorporated in each sample heated to 50° C. was studied every 5 wt. %. The wt. % prior to that where water separation occurred was designated as the value of water-absorbing capabilities. The results are shown in Table 1.

TABLE 1

|  |  | Example invention products | | | Comparative products | | | | | (wt. %) |
|---|---|---|---|---|---|---|---|---|---|
| No. of oil or fat composition | | 1 | 2 | 3 | 4 | 5 | 6 | 7 | 8 |
| Composition of oil or fat[*1] | TG | 0 | 0 | 0 | 96.3 | 15.5 | 0 | 0 | 0 |
| | DG | 7 | 5 | 2 | 1.2 | 83.7 | 7.9 | 0 | 0 |
| | MG | 93 | 94.9 | 96.4 | 0.5 | 0.8 | 92.1 | 0 | 0 |
| | FFA | 0 | 0.1 | 1.6 | 0 | 0 | 0 | 100 | 100 |

TABLE 1-continued (wt. %)

| | No. of oil or fat composition | Example invention products | | | Comparative products | | | | |
|---|---|---|---|---|---|---|---|---|---|
| | | 1 | 2 | 3 | 4 | 5 | 6 | 7 | 8 |
| Composition of fatty acid | C16:0 | 17 | 9.9 | 3.2 | 17 | 2.6 | 5.5 | ND | ND |
| | C16:1 | 4.7 | 3.5 | ND*² | 4.7 | 0.5 | 0.3 | ND | ND |
| | C18:0 | 4.1 | 2 | 1.7 | 4.1 | 1.5 | 4.1 | ND | ND |
| | C18:1 | 22.6 | 11.1 | 0.3 | 22.6 | 0.3 | 69.9 | ND | ND |
| | C18:2 | 1 | 1.6 | 0.7 | 1 | 0.6 | 14.2 | ND | ND |
| | C20:1 | 2.9 | 1.6 | 1.2 | 2.9 | 1.1 | 1.8 | ND | ND |
| | C20:5 | 6.3 | 6.7 | 6.3 | 6.3 | 5.9 | ND | 99 | ND |
| | C22:5 | 1.6 | 2.4 | 1.2 | 1.6 | 1.6 | ND | ND | ND |
| | C22:6 | 24 | 41.3 | 63.7 | 24 | 67.2 | ND | ND | 98 |
| | DHA/IPA | 3.8 | 6.2 | 10.1 | 3.8 | 11.4 | — | — | — |
| Processability | PPARγ | 233 | 535 | 488 | 141 | 129 | 135 | 480 | 508 |
| | Gelling properties | B | A-B | A | D | D | B | D | D |
| | Rancid odor | B | A-B | A | C | D | A | D | D |
| | Water-absorbing capabilities | 20 | 25 | 35 | 0 | 0 | 10 | — | — |

*¹Composition of oil or fat: TG: triglyceride, DG: diglyceride, MG: monoglyceride, FFA: free fatty acid
*²ND: Not detected As is apparent from Table 1, it has been found that owing to high gelling properties and excellent water-absorbing capabilities, the example invention products readily form a gel having a large amount of water incorporated therein and emits little rancid odor. Accordingly, the oil or fat compositions of the present invention are excellent in processability into a variety of foods and in addition, have a good flavor. Such characteristics result in merits such as reduction in dripping upon freezing-thawing and improvement in storage stability due to the lowered water activity (Aw). The comparative products 4 and 5 having a low monoglyceride content are, on the other hand, inferior in gelling properties and therefore cannot incorporate water therein.

It has also been revealed that the example oil or fat compositions of the present invention have remarkably potent PPARγ activating effects compared with the comparative product 6 (having a high monoglyceride content, but different in the composition of the fatty acid).

Example 6

Animal Test (Test on β Oxidation Activation)

An animal feed obtained by adding 10 parts by weight of the Oil or Fat Composition 2 (Example invention product) or Oil or Fat Composition 6 (comparative product) to a basic diet having the composition as shown in Table 2 was fed to C57BL/6 mice (n=6) for 10 days. On the last day, they were dissected and from the small intestine, mRNA was isolated. The amount of expression of mRNA of ACO (Acyl-CoA Oxidase) was measured in accordance with the Real time RT-PCR method. In Table 3, the results are shown in terms of a relative amount supposing that the amount of expression of mRNA when the oil or fat composition 6 was fed was set at 1.00.

TABLE 2

| Composition of basic diet | Parts by weight |
|---|---|
| Fat*¹ | 20.0 |
| Sucrose | 13.0 |
| Casein | 20.0 |
| Cellulose | 4.0 |
| Mineral*² | 3.5 |

TABLE 2-continued

| Composition of basic diet | Parts by weight |
|---|---|
| Vitamin*³ | 1.0 |
| Potato starch | 28.5 |

*¹high linoleic safflower oil + rapeseed oil + perilla oil (weight ratio = 47.0: 48.9:4.1)
*²AIN-76 prescription
*³AIN-76 prescription + choline bitartrate (20 g/100 g)

TABLE 3

| Oil or fat composition | amount of expression of mRNA (relative value) |
|---|---|
| 2 (Example invention product) | 2.12 ± 0.66 |
| 6 (Comparative product) | 1.00 ± 0.45 |

The intake of the Oil or Fat Composition 2 of the present invention caused a marked increase in the amount of expression mRNA of ACO, a β-oxidation-related enzyme, in the small intestine, showing that it promoted activation of β oxidation.

Example 7

Tablets

An Oil or Fat Composition 7 was obtained by mixing 100 parts by weight of the Oil or Fat Composition 2, 0.02 part by weight of "Mix Vitamin E MDE-6000" (product of Yashiro), 0.1 part by weight of "Sunkatol No.1" (catechin, product of Taiyo Kagaku), 0.02 part by weight of "Vitamin C palmitate (product of Roche), and 2.0 parts by weight of "CANOLA STERYLESTERS" (phytosterol, product of ADM). A mixture of 10 parts by weight of the resulting oil or fat composition, 44 parts by weight of corn starch, 40 parts by weight of crystalline cellulose, 5 parts by weight of carboxymethylcellulose calcium, 0.5 part by weight of silicic anhydride and 0.5 part by weight of magnesium stearate was compressed into tablets (200 mg/tablet).

Example 8

Soft Capsules

An Oil or Fat Composition 8 was prepared by mixing 100 parts by weight of the Oil or Fat Composition 3, 0.02 part by weight of "Mix Vitamin E MDE-6000" (product of Yashiro), 0.5 part by weight of "Sunkatol No.1" (catechin, product of Taiyo Kagaku), 0.1 part by weight of "Herbalox type HT-O" (rosemary extract, product of KALSEC, INC) and 0.2 part by weight of "THL-3" (polyglycerin fatty acid ester, product of Sakamoto Yakuhin Kogyo). The resulting oil or fat composition (300 mg) was encapsulated in oval type capsules, whereby soft capsules were prepared.

Example 9

Fried Fish Balls

In a food processor, 6 parts by weight of the Oil or Fat Composition 1, 600 parts by weight of Alaska Pollack (fish paste), 30 parts by weight of sugar, 30 parts by weight of soy sauce, 5 parts by weight of sweet cooking rice wine, 5 parts by weight of potato starch and 100 parts by weight of a whole egg were stirred and mixed vigorously. After 50 g portions of the resulting mixture were shaped into oblong pieces, they were deep fried for 4 minutes in salad oil (product of Nisshin Oillio) heated at 180° C., whereby fried fish balls were prepared.

Example 10

Spread

An oil phase: 0.5 part by weight of the Oil or Fat Composition 2, 68.8 parts by weight of partially hydrogenated soybean oil, 0.1 part by weight of lecithin, 0.5 part by weight of condensed ricinoleate, and 0.1 part by weight of a flavor.

An aqueous phase: 28.4 parts by weight of water, 0.3 part by weight of powdered skim milk, and 1.3 parts by weight of salt.

The above-described oil phase and aqueous phase were prepared, and they were mixed and emulsified in a homomixer (manufactured by Tokushu Kika Kogyo) for 10 minutes. The resulting emulsion was quenched and plasticized in a manner known per se in the art, whereby a spread was prepared.

Example 11

Pet food

A dog food was prepared by mixing 2 parts by weight of the Oil or Fat Composition 7, 15 parts by weight of corn powder, 8 parts by weight of meat meal, 26 parts by weight of wheat flour, 20 parts by weight of defatted soybean, 16 parts by weight of fish powder, 4 parts by weight of beat pulp, 2 parts by weight of bone powder, 4 parts by weight of a vitamin-mineral mixture and 3 parts by weight of lard.

The preferred oil or fat compositions according to the present invention are excellent in processability, have a good flavor, and are excellent in PPAR activating effects and β oxidation activating effects so that they are beneficial as foods and animal feed as well as pharmaceuticals for diabetes, hyperlipidemia and obesity.

The invention claimed is:

1. An oil or fat composition comprising the following components (A) and (B):
    (A) from 80 to 99.9 wt. % of a monoglyceride comprising 20 to 75 wt. % of docosahexaenoic acid (DHA) and 0.1 to 25 wt. % of icosapentaenoic acid (IPA), as the constituent fatty acids thereof, wherein the weight ratio of DHA/IPA is 2 or more, and
    (B) from 0.1 to 20 wt. % of a diglyceride.

2. The oil or fat composition of claim 1, further comprising (C) from 0.01 to 5 wt. % of an antioxidant.

3. The oil or fat composition of claim 2, wherein the antioxidant is any one of ingredients selected from catechin, tocopherol, vitamin C fatty acid esters, butylated hydroxytoluene (BHT), butylated hydroxyanisole (BHA), tertiary butylated hydroquinone (TBHQ), phospholipids and natural antioxidant components, or a mixture composed of two or more of these ingredients.

4. The oil or fat composition of claim 2, wherein the antioxidant is catechin, tocopherol, or a mixture thereof.

5. The oil or fat composition of claim 1, further comprising (D) from 0.05 to 19.9 wt. % of a phytosterol.

6. The oil or fat composition of claim 1, wherein the content of DHA is from 30 to 65 wt. %.

7. The oil or fat composition of claim 1, wherein the content of DHA is from 35 to 55 wt. %.

8. The oil or fat composition of claim 1, wherein the content of IPA is from 0.1 to 20 wt. %.

9. The oil or fat composition of claim 1, wherein the content of IPA is from 0.1 to 15 wt. %.

10. The oil or fat composition of claim 1, wherein the weight ratio of DHA/IPA is from 2 to 20.

11. The oil or fat composition of claim 1, wherein the weight ratio of DHA/IPA is from 3 to 13.

12. The oil or fat composition of claim 1, wherein the weight ratio of DHA/IPA is from 4 to 11.

13. The oil or fat composition of claim 1, wherein the weight ratio of DHA/IPA is from 5 to 8.

14. The oil or fat composition of claim 1, wherein the weight percent of monoglyceride as component (A) is from 90 to 99 wt. % and the weight percent of diglyceride as component (B) is from 1 to 10 wt. %.

15. The oil or fat composition of claim 1, wherein the content of the free fatty acids of the monoglyceride is 5 wt. % or less.

16. The oil or fat composition of claim 1, wherein the content of the free fatty acids of the monoglyceride is from 0 to 2.5 wt. %.

17. A food comprising the oil or fat composition as claimed in claim 1.

18. An animal feed comprising the oil or fat composition as claimed in claim 1.

19. A pharmaceutical comprising the oil or fat composition as claimed in claim 1.

* * * * *